United States Patent [19]

Glowczewskie, Jr. et al.

[11] Patent Number: 4,863,473
[45] Date of Patent: Sep. 5, 1989

[54] OSTEOPROSTHESIS FOR CADAVER, AND METHOD

[75] Inventors: Frank P. Glowczewskie, Jr., Gainesville, Fla.; Alfred A. Litwak, Sea Bright, N.J.; Jamie M. Grooms, Atlantic Highlands, N.J.; John W. Lyle, Belmar, N.J.

[73] Assignee: Osteotech, Inc., Shrewsbury, N.J.

[21] Appl. No.: 178,248

[22] Filed: Apr. 6, 1988

[51] Int. Cl.⁴ .............................................. A61F 2/28
[52] U.S. Cl. ...................................... 623/16; 623/66; 128/92 ZZ; 27/21.1; 248/188.5; 248/546
[58] Field of Search ................... 623/16, 18–20, 623/38, 66, 28; 434/267, 274, 275, 296; 27/21.1; 128/92 R, 92 ZZ, 92 ZY, 92 Y, 92 YZ, 92 YY, 92 YV; 248/57, 188.5, 546, 251, 257, 260, 261, 264, 265, 268–272, 71

[56] References Cited

U.S. PATENT DOCUMENTS

| | | | |
|---|---|---|---|
| 2,672,861 | 3/1954 | Jonas et al. | 128/92 YZ |
| 3,176,851 | 4/1965 | Mueller | 248/57 X |
| 3,400,408 | 9/1968 | Garcia | 623/38 X |
| 4,096,857 | 6/1978 | Cramer et al. | 128/92 ZY X |
| 4,308,863 | 1/1982 | Fischer | 128/92 ZZ |
| 4,586,932 | 5/1986 | Scales | 623/16 |
| 4,621,627 | 11/1986 | DeBastiani et al. | 128/92 ZZ |
| 4,659,051 | 4/1987 | Propp et al. | 248/546 |

FOREIGN PATENT DOCUMENTS 0451768  3/1950  Italy .................................. 623/38

Primary Examiner—Richard J. Apley
Assistant Examiner—David J. Bender
Attorney, Agent, or Firm—Dilworth & Barrese

[57] ABSTRACT

A prosthesis for replacing bone extracted from a cadaver. A preferred prosthesis is formed of two tubes of differing diameter, the larger-diameter tube beng slidable over the smaller-diameter tube to provide a telescoping assembly. A stop is provided on the smaller tube, and is adjustably positioned thereon for operatively contacting an end of the larger tube to resist contraction of the assembly after insertion within a cadaver. Threaded pins are provided at the ends of the assembly for engagement within bone of a skeleton of the cadaver. The prosthesis retains the physical appearance of a cadaver after extraction of bone for use in surgical and other therapeutic purposes on living organisms.

11 Claims, 3 Drawing Sheets

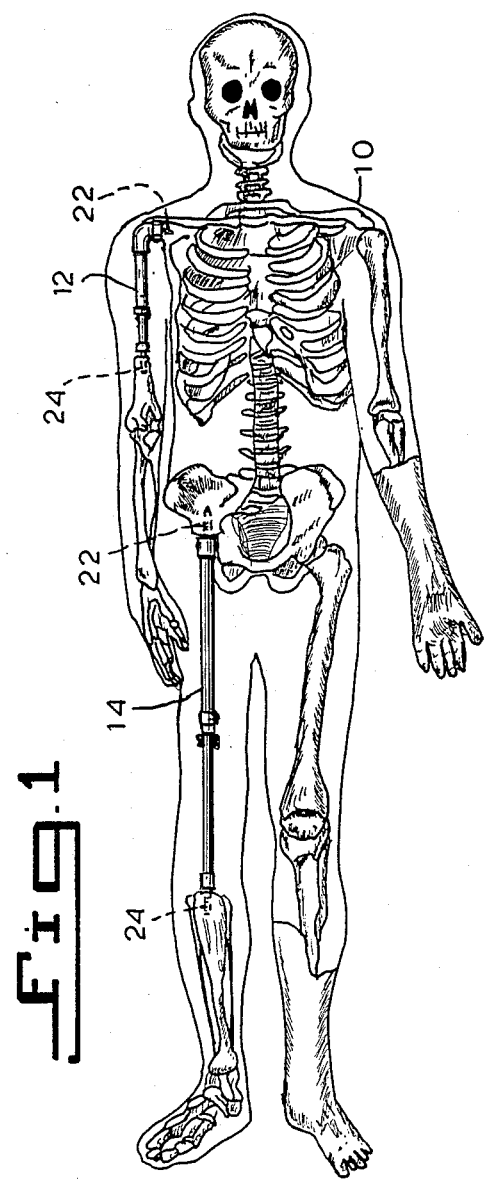

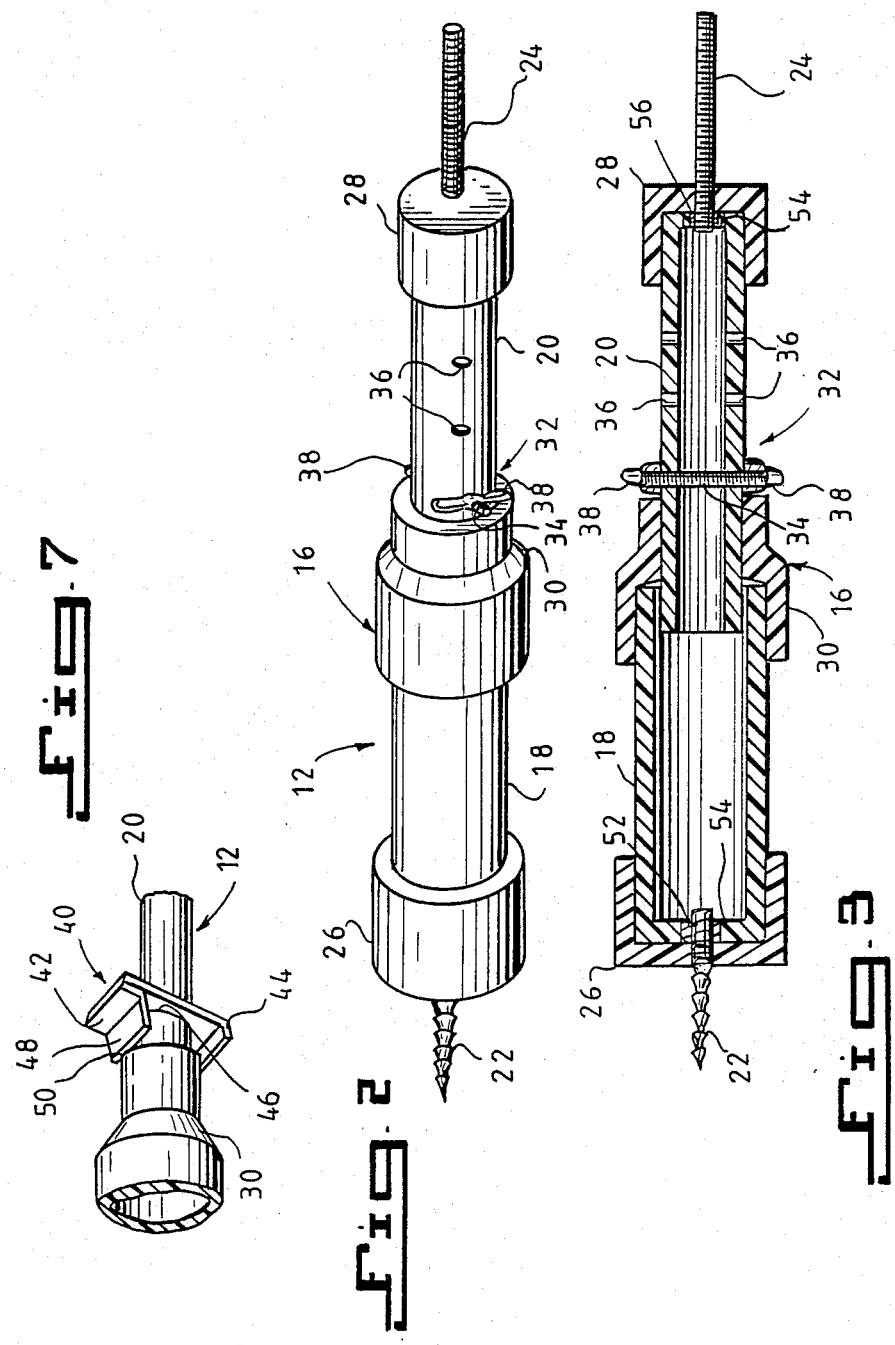

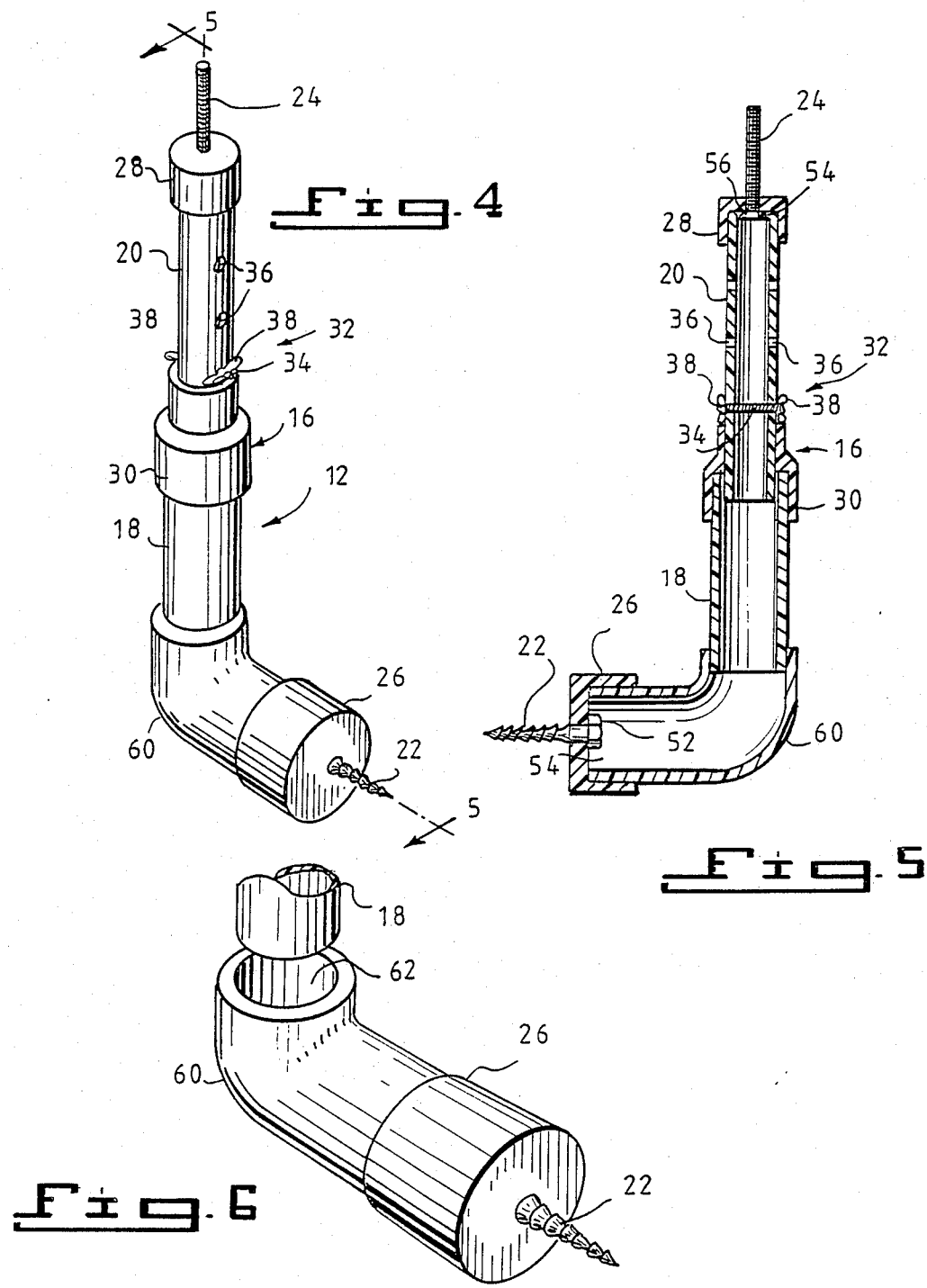

OSTEOPROSTHESIS FOR CADAVER, AND METHOD

BACKGROUND OF THE INVENTION

This invention relates to an osteoprosthesis to replace extracted bone material from cadavers for use as transplants n human beings and, more particularly, to an osteoprosthesis useful for the preservation of the form of the cadaver by insertion of the prosthesis at the location occupied by the extracted bone material.

The use of bone material extracted from one human being for use as a transplant in another human being is accomplished by a surgical procedure which is most useful in curing certain diseases and abnormalities. The bone material is obtained from a human being shortly after the human being has been declared dead. Therefore, the procurement of the bone material necessitates the invasion of a cadaver.

A problem arises in that the invasion of the cadaver may result in the deformation or distortion of a limb of the cadaver. Such mutilation in the appearance of the cadaver can be a source of a considerable anguish to the bereaved who are mourning the death of a loved one. In order to secure permission of the bereaved to release the cadaver for extraction of bone material, it is necessary to handle the cadaver in a fashion which, after extraction of the bone material, preserves the form of the cadaver and, in particular, avoids the appearance of any mutilation associated with the deformation or distortion of a limb.

SUMMARY OF THE INVENTION

The foregoing problem is overcome, and other advantages are provided by an osteoprosthesis, or bone prosthesis which, in accordance with the invention, occupies the space from which the bone material has been extracted, and provides sufficient rigidity to the limb from which the bone has been extracted to retain the form of the limb.

The invention provides for the construction of the prosthesis in the form of a telescoping assembly having mechanical stops thereon to secure a predetermined length to the prosthesis, the length being commensurate with the length of an extracted bone or bone portion. A preferred embodiment of the prosthesis is fabricated of two cylindrical tubular members or elements, one being of smaller diameter than the other, the smaller-diameter tube being fit within the larger-diameter tube to provide for a telescoping action. To insure adequate strength in an elongated position of the tubes and preventing the tubes from accidentally separating when tilting the small tube end down, the outer tube is provided with a collar which encircles the end of the tube at its juncture with the smaller-diameter tube. While the preferred telescoping assembly of the present invention is comprised of tubular or dowel like elements, other rod-like or rod-shaped elements or members used in place of or in conjunction with said tubular elements are clearly within the scope of the invention herein.

Both ends of the prosthesis are provided with pins to be inserted within bones of the skeletal portions at opposite ends of the region of extracted bone. The pins are provided with a sufficient length and diameter to secure the device within a hollow portion of a bone, or may be provided with a self-tapping thread to permit threaded engagement with a solid piece of bone. A stop used in securing the inner and outer tubes at a predetermined length is formed with a peg passing through holes in a tube, the peg being secured after attachment of the end pins of the prosthesis to the respective portions of the skeleton. The stops prevent a contraction of the prosthesis. Elongation of the prosthesis is prevented by musculature and other body fibers of the cadaver. A stop may also be constructed as a sliding jam collar which encircles the smaller-diameter tube and rests against the collar of the larger-diameter tube.

BRIEF DESCRIPTION OF THE DRAWING

The foregoing aspects and other features of the invention are explained in the following description, taken in connection with the accompanying drawing wherein:

FIG. 1 is a stylized view of a cadaver showing the prosthesis of the invention replacing bone which has been extracted from the skeleton of a cadaver;

FIG. 2 is a perspective view of one embodiment of the prosthesis of the invention;

FIG. 3 is a longitudinal sectional view of the prosthesis of FIG. 2;

FIG. 4 is a perspective view of another embodiment of the prosthesis of the invention;

FIG. 5 is a longitudinal sectional view of the prosthesis of FIG. 4 taken along line 5—5;

FIG. 6 is an enlarged, partly exploded view of the prosthesis of FIG. 4; and

FIG. 7 is a fragmentary view of the prosthesis showing an alternative embodiment of a stop.

DETAILED DESCRIPTION OF THE INVENTION

With reference to FIG. 1, there is shown a cadaver 10 in which bone material from the right arm and from the right leg have been extracted. In the arm, the extracted material has been replaced with a prosthesis 12 which is constructed as a relatively short embodiment of the invention. Substantially more bone material has been removed from the leg and, accordingly, this bone material has been replaced with a prosthesis 14 which is constructed as a substantially longer embodiment of the invention. The basic principles of construction, in accordance with the invention, are the same in both the prosthesis 12 and the prosthesis 14.

With reference also to FIGS. 2, 3, 4, 5 and 6 there is shown further detail in the construction of the prosthesis 12, it being understood that the constructional details apply equally well to the prosthesis 14. The prosthesis 12 is formed as a telescoping assembly 16 formed of a first tube 18, and a second tube 20 having a smaller diameter than the first tube 18 so as to fit slidably within the first tube 18. A first end of the assembly 16 is formed at an outer end of the tube 18 and includes a first end 22 having a self-tapping screw thread. The opposite end of the assembly 16 is formed at an outer end of the second tube 20 and includes a second pin 24 configured as a threaded bolt.

The bone material removed from the arm of the cadaver 10 is shown, by way of example, as an upper portion of the humerus. The pin 24 is readily secured to the remaining portion of the humerus by inserting the pin 24 within the marrow. If desired, the pin 24 may be provided with rings of teeth (not shown) or other gripping surface or may be a smooth surface pin in lieu of the bolt thread shown in the drawing. On the other hand, the pin 22 at the opposite end of the prosthesis 12 must be passed into solid bone, such as the clavicle or other suitable solid bone. The self-tapping screw thread of the pin 22 is readily secured within the bone material of the clavicle by rotating the tube 18 relative to the tube 20 so as to thread the pin 22 into the clavicle. The slidable mounting of the tube 20 within the tube 18 permits independent rotation of one tube relative to the other tube in addition to translation of one tube relative to the other tube. Thereby, the two tubes 18 and 20 may be secured by their respective pins 22 and 24 to the clavicle and the humerus, the assembly 16 being extended a sufficient amount to equal the length of extracted bone material from the humerus. Similarly, in the case of the extraction of bone material from the leg of the cadaver 10, by way of example, an upper portion of the tibia and fibula have been removed along with the patella and the femur. As in the case of the prosthesis 12, the prosthesis 14 is also provided with pins 22 and 24, the pin 24 being secured within marrow of the tibia, and the pin 22 being secured within solid bone material, the os coxa surrounding the hip joint. The two tubular portions of the prosthesis 14 can be translate and rotate relative to each other, in the same fashion as has been described for the prosthesis 12 so as to accommodate the length of bone material extracted from the leg of the cadaver 10, and to allow rotation of the pins 22 and 24 for securing these pins into the remaining bone material of the skeleton of the cadaver 10.

The prosthesis 12 further comprises end caps 26 and 28 disposed on the outer ends of the tubes 18 and 20 for strengthening the ends of the assembly 16. In the central portion of the assembly 16, a junction of the two tubes 18 and 20 is strengthened by means of a collar 30 which is secured to the inner end of the tube 18, and tapers to a smaller diameter for enveloping an inner end portion of the tube 20. The collar 30 is provided with an inner diameter which closely matches the outer diameter of the tube 20, the two diameters being substantially equal except for a small clearance necessary to facilitate sliding of the tube 20 within the collar 30.

FIG. 4 illustrates a preferred embodiment of the prosthesis, particularly the arm prosthesis 12, of the present invention. In this embodiment, a separable elbow 60, preferably a 90° elbow (although other angle elbows are also contemplated herein), with end cap 26 and first end 22 having a self-tapping screw thread, is provided. Elbow 60 is provided with an open end having an opening 62 having a diameter slightly greater than first tube 18 thereby allowing first tube 18 to be snugly fitted within the opening 62 of elbow 60. Thus, in the utilization of the embodiment of FIG. 4, elbow 60 with end cap 26 and first end 22 is first secured via self-tapping screw 22 within the bone material of the clavicle or other suitable bone material by rotating the elbow 60 so as to thread the screw 22 into the bone. After securement of elbow 60 into the bone, first tube 18 is inserted into opening 62 of elbow 60 and after extending assembly 16 to a sufficient length to equal the length of extracted bone, pin 24 is inserted into the marrow of the humerus.

When the prosthesis 12 is inserted within the arm, and similarly with the insertion of the prosthesis 14 in the leg, the flesh and musculature of the cadaver 10 prevent further elongation of the prosthesis. However, in order to prevent contraction of the prosthesis 12 after insertion, the prosthesis 12 is provided with a stop 32 composed of a threaded peg 34 passing between a pair of diametrically opposed apertures 36 in the second tube 20 and being secured thereto by wing nuts 38. Three pairs of opposed apertures 36 are shown in FIGS. 2 and 4 for the construction of the prosthesis 12, it being understood that many more of the pairs of apertures 36 are provided in the longer prosthesis 14. The wing nuts 38 abut the end of the collar 30 to prevent a contractile telescoping of the assembly 16. The peg 34 may be inserted in any one of the pairs of diametrically opposed apertures 36 to adjust the prosthesis to a desired length.

In FIG. 7 the fragmentary view of the prosthesis 12 shows a stop 40 which is an alternative embodiment to the stop 32 of FIGS. 2 and 3. The stop 40 comprises a jam collar 42 formed as a plate 44 having an aperture 46 therein, and a leg 48 extending from the plate 44 adjacent the aperture 46. The leg 48 is angled relative to a normal to the plate 44. The tube 20 passes through the aperture 46 the inner periphery of which grips tube 20. The leg 48 is pushed by the collar 30 causing the stop 40 at its outer end 50 to abut against the collar 30 so as to prevent a contractile telescoping of the prosthesis. The stop 40 is released upon any telescopic elongation of the prosthesis.

The following parameters are employed in the construction of a preferred embodiment of the invention. With respect to the tubes 18 and 20 employed in the construction of the leg prosthesis 14, maximum tube diameter is one inch and minimum tube diameter is $\frac{1}{2}$ inch. The prosthesis 14 is expandable in a range from 23 inches to 36 inches. The length is adjustable in steps of 1 inch. In a fully extended configuration, the prosthesis 14 can withstand a torque of 2 pounds acting at a distance of 36 inches. The foregoing parameters for the case of the arm prosthesis 12 are as follows. Maximum tubular diameter is 1 inch and minimum tubular diameter is $\frac{1}{4}$ inch. The prosthesis 12 telescopes over a range from 5 inches to 6 $\frac{1}{2}$ inches The length is adjustable in steps of $\frac{3}{4}$ inch. Upon full extension, the prosthesis 12 can withstand a torque of two pounds acting at a distance of 6 $\frac{1}{2}$ inches. Other lengths however are obviously contemplated herein.

The pin 22 is formed of a hangar bolt (#10) which extends outwardly from the end cap 28 a distance of approximately 1 inch in the case of the prosthesis 14, and $\frac{3}{4}$ of an inch in the case of the prosthesis 12. These bolts enable the prosthesis to support 4 pounds of lateral force, 10 pounds of compressive force, two pounds of tensile force, and 5 pound-feet of torque about a longitudinal axis of the prosthesis.

The pin 24 has a diameter of approximately 3/16 of an inch and a length of approximately 2 inches. The pin 24 enables the prosthesis to support 4 pounds of lateral force and 2 pounds of compressive force. The prosthesis can be expanded upon use of a force within the range of 0.1 pounds to 5 pounds.

The material employed in the construction of the osteoprosthesis assembly of the invention, such as in the construction of tubes 18 and 20, as well as in the caps 26 and 28, elbow 60 and the collar 30 is, preferably for example, a polymerized plastic material, e.g., polyvinylchloride. Other materials, such as metal and/or wood may also be used however. The pin 22 is secured to the end of the assembly 16 with the aid of a tee nut 52 secured to the outer end of the tube 18 with a plastic binder or adhesive 54 which extends from the inner surface of the tube 18 to provide a mating configuration of the end of the tube 18 for mating with the nut 52, thereby to lock the nut 52 into position. The cap 26 is secured to the outer surface of the tube 18 or the outer surface of the elbow 60 with an adhesive. Similarly, the larger diameter portion of the collar 30 is secured to the outer surface of the tube 18 with an adhesive. The pin 24 is secured to the outer end of the tube 20 means of a nut 56 which is held in position by a plastic binder or adhesive 54 which extends from the inner surface of the tube 20 to form a mating configuration to the nut 54. The cap 28 is secured to the outer surface of the tube 20 by an adhesive. Adequate strength in the joining of the pin 22 to the assembly 16 is provided by both the cap 26, through which the pin 22 passes, as well as by the nut 52 secured to the tube 18 or nut 52 secured to elbow 60. Adequate strength in the joining of the pin 24 to the assembly 16 is provided by both the cap 28, through which the pin 24 passes, as well as by the nut 56 secured to the tube 20.

The foregoing structure provides for a light weight, easily manufactured osteoprosthesis which is readily inserted in a cadaver to maintain normal appearance after extraction of bone material.

It is to be understood that the above described embodiments of the invention are illustrative only, and that modifications thereof may occur to those skilled in the art. Accordingly, this invention is not to be regarded as limited to the embodiment disclosed herein, but is to be limited only as defined by the appended claims.

What is claimed is:

1. An osteoprosthesis for a cadaver comprising:
   a first tube and a second tube, the first tube having a larger diameter than the second tube and being slidably mounted on the second tube to form therewith a telescoping assembly, each tube within said assembly having an inner end and an outer end, the inner ends of the tubes being disposed at a central portion of said assembly, outer ends of the tubes forming outer ends of the assembly, each of said tubes being circular cylinders;
   a first pin mounted in an outer end of said first tube, and a second pin mounted in an outer end of said second tube, each of said pins being configured for engagement with bone;
   an adjustable stop engaging said first and said second tubes, said stop permitting adjustment of the length of said assembly for affixing said pins to bones, said stop limiting a contracting of said assembly to a minimum length subsequent to affixation of said pins to bones;
   a collar disposed around an inner end of said first tube for secure engagement with said second tube;
   end caps at outer ends of said tubes for securing said pins to respective ones of said tubes; and wherein
   at least one of said end caps includes a nut threadedly secured to a pin;
   at least one of said pins are provided with screw threads for engagement with bone;
   the tubes within said assembly are rotatable relative to each other to permit rotation of a screw thread of a pin within bone; the prosthesis further comprising
   stop means operatively coupled to said first tube and said second tube for resisting contraction of said assembly upon affixation of said ends to bones, said stop means being adjustable, said stop means being releasable during insertion of said pins in bones; and wherein
   said stop means comprises a jam collar encircling said second tube, said stop means being activated upon a pressing of said stop means against the collar disposed around said first tube.

2. An osteoprosthesis according to claim 1 wherein each of said tubes is formed of a plastic material and each of said pins is formed of a metal.

3. An osteoprosthesis according to claim 1 wherein at least one of said outer ends of at least one of said tubes comprises an elbow member.

4. An osteoprosthesis according to claim 3 wherein said elbow is a 90° elbow.

5. An osteoprosthesis for a cadaver comprising;
   a first tube and a second tube, the first tube having a larger diameter than the second tube and being slidably mounted on the second tube to form therewith a telescoping assembly, each tube within said assembly having an inner end and an outer end, the inner ends of the tubes being disposed at a central portion of said assembly, outer ends of the tubes forming outer ends of the assembly, each of said tubes being circular cylinders;
   a first pin mounted in an outer end of said first tube, and a second pin mounted in an outer end of said second tube, each of said pins being configured for engagement with bone;
   an adjustable stop engaging said first and said second tubes, said stop permitting adjustment of the length of said assembly for affixing said pins to bones, said stop limiting a contracting of said assembly to a minimum length subsequent to affixation of said pins to bones;
   a collar disposed around an inner end of said first tube for secure engagement with said second tube;
   end caps at outer ends of said tubes for securing said pins to respective ones of said tubes; and wherein
   at least one of said end caps includes a nut threadedly secured to a pin;
   at least one of said pins are provided with screw threads for engagement with bone;
   the tubes within said assembly are rotatable relative to each other to permit rotation of a screw thread of a pin within bone; the prosthesis further comprising
   stop means operatively coupled to said fist tube and said second tube for resisting contraction of said assembly upon affixation of said ends to bones, said stop means being adjustable, said stop means being releasable during insertion of said pins in bones; and wherein
   said stop means is configured as a set of apertures disposed in said second tube, said stop means including peg means insertable into an aperture of said set of apertures for contacting said collar at the inner end of said first tube during operation of said stop means;
   said peg means is a bolt threading a diametrically opposed pair of said apertures in said stop means, there being wing-nut means disposed on said bolt for securing said bolt to said second tube;
   said apertures are arranged serially along an axis of said second tube to permit a selection of apertures to establish a desired length of said assembly.

6. An osteoprosthesis according to claim 5 wherein each of said tubes is formed of a plastic material and each of said pins is formed of a metal.

7. An osteoprosthesis according to claim 5 wherein said outer end of said first tube comprises an elbow member.

8. An osteoprosthesis according to claim 7 wherein said elbow is a 90° elbow.

9. A process for the restoration of the form of a cadaver wherein bone has been extracted from said cadaver, said process comprising inserting an osteoprosthesis at the location occupied by the extracted bone, said osteoprosthesis comprising:
- a first member, and a second member mounted thereto to form a telescoping assembly, each member of said assembly having an inner end and an outer end, the inner ends of the members being disposed at a central portion of said assembly, the outer ends of the members forming outer ends of the assembly;
- a first pin mounted in an outer end of said first member, and a second pin mounted in an outer end of said second member, each of said pins being configured for engagement with bone; and
- an adjustable stop engaging said first and said second members, said stop permitting adjustment of the length of said assembly for affixing said pins to bones, said stop limiting a contracting of said assembly to a minimum length subsequent to affixation of said pins to bones, said process further including the step of adjusting the length of said telescoping assembly to compensate for the length of said extracted bone.

10. A process for the restoration of the form of a cadaver wherein bone has been extracted from said cadaver, said process comprising inserting an osteoprosthesis at the location occupied by the extracted bone, said osteoprosthesis comprising:
- a first tube and a second tube, the first tube having a larger diameter than the second tube and being slidably mounted on the second tube to form therewith a telescoping assembly, each tube within said assembly having an inner end and an outer end, the inner ends of the tubes being disposed at a central portion of said assembly, outer ends of the tubes forming outer ends of the assembly, each of said tubes being circular cylinders;
- a first pin mounted in an outer end of said first tube, and a second pin mounted in an outer end of said second tube, each of said pins being configured for engagement with bone;
- an adjustable stop engaging said first and said second tubes, said stop permitting adjustment of the length of said assembly for affixing said pins to bones, said stop limiting a contracting of said assembly to a minimum length subsequent to affixation of said pins to bones;
- a collar disposed around an inner end of said first tube for secure engagement with said second tube;
- end caps at outer ends of said tubes for securing said pins to respective ones of said tubes; and wherein
- at least one of said end caps includes a nut threadedly secured to a pin;
- at least one of said pins are provided with screw threads for engagement with bone;
- the tubes within said assembly are rotatable relative to each other to permit rotation of a screw thread of a pin within bone; the prosthesis further comprising
- stop means operatively coupled to said first tube and said second tube for resisting contraction of said assembly upon affixation of said ends to bones, said stop means being adjustable, said stop means being releasable during insertion of said pins in bones; and wherein
- said stop means comprises a jam collar encircling said second tube, said stop means being activated upon a pressing of said stop means against the collar disposed around said first tube, said process further including the step of adjusting the length of said telescoping assembly to compensate for the length of said extracted bone.

11. A process for the restoration of the form of a cadaver wherein bone has been extracted from said cadaver, said process comprising inserting an osteoprosthesis at the location occupied by the extracted bone, said osteoprosthesis comprising:
- a first tube and a second tube, the first tube having a larger diameter than the second tube and being slidably mounted on the second tube to form therewith a telescoping assembly, each tube within assembly having an inner end and an outer end, the inner ends of the tubes being disposed at a central portion of said assembly, outer ends of the tubes forming outer ends of the assembly, each of said tubes being circular cylinders;
- a first pin mounted in an outer end of said first tube, and a second pin mounted in an outer end of said second tube, each of said pins being configured for engagement with bone;
- an adjustable stop engaging said first and said second tubes, said stop permitting adjustment of the length of said assembly for affixing said pins to bones, said stop limiting a contracting of said assembly to a minimum length subsequent to affixation of said pins to bones;
- a collar disposed around an inner end of said first tube for secure engagement with said second tube;
- end caps at outer ends of said tubes for securing said pins to respective ones of said tubes; and wherein
- at least one of said end caps includes a nut threadedly secured to a pin;
- at least one of said pins are provided with screw threads for engagement with bone;
- the tubes within said assembly are rotatable relative to each other to permit rotation of a screw threaded of a pin within bone; the prosthesis further comprising
- stop means operatively coupled to said first tube and said second tube for resisting contraction of said assembly upon affixation of said ends to bones, said stop means being adjustable, said stop means being releasable during insertion of said pins in bones; and wherein
- said stop means is configured as a set of apertures disposed in said second tube, said stop means including peg means insertable into an aperture of said set of apertures for contacting said collar at the inner end of said first tube during operation of said stop means;
- said peg means is a bolt threading a diametrically opposed pair of said apertures in said stop means, there being wing-nut means disposed on said bolt for securing said bolt to said second tube;
- said apertures are arranged serially along an axis of said second tube to permit a selection of apertures to establish a desired length of said assembly, said process further including the step of adjusting the length of said telescoping assembly to compensate for the length of said extracted bone.

* * * * *